United States Patent [19]

Cohen

[11] Patent Number: 5,330,505
[45] Date of Patent: Jul. 19, 1994

[54] SYSTEM FOR AND METHOD OF TREATING A MALFUNCTIONING HEART

[75] Inventor: Todd J. Cohen, Port Washington, N.Y.

[73] Assignee: Leonard Bloom, Towson, Md.; a part interest

[21] Appl. No.: 879,909

[22] Filed: May 8, 1992

[51] Int. Cl.$^5$ .......................................... A61N 1/365
[52] U.S. Cl. ......................................... 607/6; 607/3
[58] Field of Search .................... 128/419 PG, 419 D

[56] References Cited

U.S. PATENT DOCUMENTS

| | | | |
|---|---|---|---|
| 3,942,536 | 3/1976 | Mirowoski et al. | 128/419 D |
| 4,184,493 | 1/1980 | Langer et al. | 128/419 D |
| 4,197,854 | 4/1980 | Kasa | 128/630 |
| 4,202,340 | 5/1980 | Langer et al. | 128/419 D |
| 4,393,877 | 7/1983 | Imran et al. | 128/705 |
| 4,475,551 | 10/1984 | Langer et al. | 128/419 D |
| 4,770,177 | 9/1988 | Schroepple | 128/419 PG |
| 4,774,950 | 10/1988 | Cohen | 128/419 D |
| 4,830,006 | 5/1989 | Haluska et al. | 128/419 PG |
| 4,846,195 | 7/1989 | Alt | 128/419 PG |
| 4,895,151 | 1/1990 | Grevis et al. | 128/419 PG |
| 4,899,751 | 2/1990 | Cohen | 128/419 PG |
| 4,899,752 | 2/1990 | Cohen | 128/419 PG |
| 4,967,748 | 11/1990 | Cohen | 128/419 D |
| 4,967,749 | 11/1990 | Cohen | 128/419 PG |
| 4,984,572 | 1/1991 | Cohen | 128/419 D |
| 4,986,270 | 1/1991 | Cohen | 128/419 D |
| 5,002,052 | 3/1991 | Haluska | 128/419 PG |
| 5,014,698 | 5/1991 | Cohen | 128/419 D |
| 5,027,816 | 7/1991 | Cohen | 128/419 PG |
| 5,054,485 | 10/1991 | Cohen | 128/419 D |
| 5,085,213 | 2/1992 | Cohen | 128/419 D |
| 5,097,831 | 3/1992 | Lekholm | 128/419 PG |
| 5,119,813 | 6/1992 | Cohen | 128/419 D |

OTHER PUBLICATIONS

Mirowski et al., "Recent Clinical Experience with the Automatic Implantable Cardioverter-Defibrillator"; *Medical Instrumentation,* vol. 20, 1986, pp. 285-291.
Mirowski, "The Automatic Implantable Cardioverter-Defibrillator: An Overview"; *JACC,* vol. 6, No. 2, Aug. 1985, pp. 461-466.
Cohen et al., "A Universal Microprocessor Controlled Heart Rhythm Control System", *Annual International Conference of IEEE Engineering in Medicine and Biology Society,* vol. 13, No. 2, 1991.
Cohen et al., "Mixed Venous Oxygen Saturation for Differentiating Stable from Unstable Tachycardias"; *American Heart Journal,* vol. 122, No. 3, Sep. 1991, pp. 733-740.

(List continued on next page.)

*Primary Examiner*—William E. Kamm
*Assistant Examiner*—Scott M. Getzon
*Attorney, Agent, or Firm*—Leonard Bloom

[57] ABSTRACT

A system for treating the malfunctioning heart of a patient includes means which derive at least one electrical signal from the patient's heart and means which derive at least two physiologic signals from or related to the patient's circulatory system. The physiologic signals, or functions thereof, are weighted and algebraically summed in a central processing unit, which may be a programmable microprocessor, having a RAM and a ROM, receives and responds to the at least one electrical signal and to the at least two physiologic signals. Output means, which may include a heart assist pump, pacers, drug delivery devices and cardioverting/-defibrillating apparatuses, controlled by the central processing unit provides corrective measure(s) to the patient. Heart-rate zone signals and the algebraic sum, at any given time effect selection of a particular treatment modality, if needed. Adjustable or variable baselines, against which a representation of the current, short-term magnitude of the selected physiologic parameter or parameters are provided. The variable baseline(s) is (are) a representation of the selected physiologic parameter(s) determined over a long term of greater duration than the short term over which the current magnitude(s) of the parameter(s) is (are) measured. The system may be used to carry out a method according to a corresponding series of steps.

41 Claims, 12 Drawing Sheets

OTHER PUBLICATIONS

Cohen, "A Theoretical Right Atrial Pressure Feedback Heart Rate Control System to Restore Physiologic Control to the Rate-limited Heart"; *PACE*, vol. 7, Jul.-Aug. 1984.

Cohen et al., "Hemodynamic Responses to Rapid Pacing: A Model for Tachycardia Differentiation"; *PACE*, vol. 11, Nov. 1988, Part I.

Cohen et al., "A Hemodynamically Response Antitachycardia System: Theoretical Basis for Design"; *Journal of Electrophysiology*, vol. 2, No. 4, 1988.

"A Hemodynamically Responsive Antitachycardia System—Development and Basis for Design in Humans"; Presented at the 11th Annual Scientific Session of the North American Society of Pacing and Electrophysiology, San Diego, May 31–Jun. 2, 1990; Cohen et al.

Cohen et al., "Biosensor Applications to Antitachycardia Devices"; *PACE*, vol. 14, Feb. 1991, Part II.

SYSTEM FOR AND METHOD OF TREATING A MALFUNCTIONING HEART

BACKGROUND OF THE INVENTION

1. Field of the Invention

This invention relates to a system for and method of treating a malfunctioning heart which involves, on the input side, sensing a plurality of physiologic parameters, as well as at least one electrocardiographic signal from the patient, determining the current activity level of the patient, and the weighing of physiologic signals, measured against respective baselines. The invention provides for the cardioverting/defibrillation of a malfunctioning heart, as well as the possibility of overcoming tachycardia and bradycardia manifestations without resorting to either cardioverting or defibrillating the heart.

2. Description of the Prior Art

In recent years, substantial progress has been made in pacemakers and in the development of cardioverting-/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting/-defibrillating technique is disclosed in U.S. Pat. No. 3,942,536 of Mirowski et al., the technique involving responses to a sensed peak right ventricular systolic pressure dropping below a fixed predetermined level and not returning above the predetermined level for a given period of time.

Efforts have also been directed toward developing techniques for reliably monitoring heart activity in order to determine whether cardioversion/defibrillation are desirable or necessary. Such techniques include monitoring ventricular rate or determining the presence of fibrillation on the basis of the probability density function (PDF) of an electrocardiographic signal. A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

An apparatus and method for treating tachyarrhythmias wherein the presence of a patient tachyarrhythmia is detected and a first antitachyarrhythmia therapy (antitachycardia pacing) is given at a first energy level has been proposed in U.S. Pat. No. 4,895,151. The hemodynamic condition of the patient is measured and a length of time to therapy switchover is continually derived during the application of the first antitachyarrhythmia therapy. The length of time to switchover is a function of the hemodynamic condition of the patient. When the time following detection of the patient tachyarrhythmia exceeds the length of time to switchover, a second antitachyarrhythmia therapy (a high energy shock) at a second energy level is provided. The average cardiac cycle length may be used as an indicator of the hemodynamic condition. Only a single hemodynamic parameter is utilized, at one time, in the Grevis et al. apparatus, cardiac cycle length being the parameter illustrated.

An implantable cardiac stimulator integrates the functions of bradycardia and anti-tachycardia pacing-type therapies, and cardioversion and defibrillation shock-type therapies is disclosed in U.S. Pat. No. 4,830,006 of Haluska et al. The stimulator is programmable to provide a multiplicity of hierarchical detection algorithms and therapeutic modalities to detect and treat classes of ventricular tachycardia according to position within rate range classes into which the heart rate continuum is partitioned, and thus according to hemodynamic tolerance, with backup capabilities of defibrillation and bradycardia pacing at the higher and lower regions of the rate continuum outside the range of the ventricular tachycardia classes. Aggressiveness of the therapy is increased with elapsed time and increasing heart rate and detection criteria are relaxed with increasing heart rate and thus with increasing hemodynamic intolerance of the tachycardia.

A method for detecting and treating ventricular tachyarrhythmias of a patient's heart is disclosed in U.S. Pat. No. 5,002,052 of Haluska which includes the steps of selectively dividing the heart rate continuum into regions including at least two classes of tachycardia, contiguous to each other and of progressively higher heart rate ranges, the lowest and highest of the tachycardia classes being bounded respectively by a sinus rate region and a fibrillation region of the continuum. The boundaries between the tachycardia classes and between the lowest and highest of those classes are selectively adjusted and the respective sinus rate and fibrillation regions to correspondingly adjust the rate ranges of the classes selectively detecting cardiac events anywhere within the continuum and distinguishing between normal and abnormal tachycardias. Treating a detected abnormal tachycardia with any of a multiplicity of therapy regimens of differing degrees of aggressiveness, toward terminating the detected tachycardia is proposed.

A process and apparatus for patient danger recognition and forecasting, particularly for the intensive medical care of the patient has been proposed in U.S. Pat. No. 4,197,854 to Kasa. The invention uses various variables to set up a danger function that represents the probability of occurrence of a danger condition, forms average values of the danger function throughout subsequent time periods that are shorter than the time required for a medical intervention. Formed average values with levels of increasing sequences of threshold values are compared providing an indication associated with the highest exceeded threshold value. The average values are used to set up a regression function which approximates the sequence thereof. A subsequent extrapolated value of the function is determined for the next time period that represents a forecast average value of the danger function. The extrapolated value is indicated, provided it is higher than a predetermined level. Preferably three threshold values are used in the comparing step, with magnitudes of 40, 60 and 80% of the danger function, respectively.

The U.S. Pat. No. 4,770,177 of Schroeppel discloses a pacer which paces a heart in accordance with the heart-/pacer rate needed to produce a required cardiac output while a person is exercising or undergoes emotional stress in response to changes in venous blood vessel diameter. The pacer is adapted to be implanted in a human body and has a pulse generator and control circuitry, which may be realized by a microprocessor. A pacing lead adapted to be implanted in a heart has a tip electrode adapted to engage and supply pacing pulses to a right ventricle of a heart. A piezoelectric sensor determines changes in a diameter of a vein in the human body. Computing circuitry, including the control circuitry, relates the changes in venous blood vessel diameter with the required pacing rate needed to supply a desired cardiac output, and causes the pacer to pace the heart at the required rate when the heart is not naturally paced. The pacer of Schroeppel is not combined with any cardioverter/defibrillator.

Currently antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators which is commercially available under the model designations 1500, 1510 and 1520 from Cardiac Pacemakers, Inc. whose address is: 4100 North Hamlin Avenue, St. Paul, Minn. 55164. These devices continuously monitor myocardial electrical activity, detecting ventricular tachycardia (VT) and ventricular fibrillation (VF), and delivering a shock to the myocardium to terminate the arrhythmia. This cardioverter-defibrillator has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator, *Medical Instrumentation*, Vol. 20, pages 285-291 (1986). Arrhythmias are detected by (1) a rate (R wave) sensor and (2) the probability density function (PDF) of an EKG signal which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", JACC, Vol. 6, No. 2, pages 461-466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski et al., supra, and the Mirowski, supra publications set out, in summary form, background material relating to the defibrillating/cardioverting arts against which the present invention was made to correct the ischemia (in a closed-loop fashion). Closed loop intravenous drug delivery systems have been developed (and are undergoing evaluation) for the treatment of heart failure. Such systems could be incorporated into an implantable device to permit the delivery of electrical therapy (pacing/cardioversion/defibrillation) as well as drug therapy, to correct a malfunctioning heart.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no hemodynamic parameter having been taken into consideration.

One problem with many current systems is that they function primarily as a rate-only and/or single-hemodynamic-parameter driven systems and may fire for non-malignant as well as malignant tachycardias. These firings are not benign; potentially endangering myocardium, wasting energy and inflicting pain on the conscious patient, all distinct shortcomings and disadvantages.

External ST segment monitoring systems are commercially available. These systems compare the normal or baseline ST segment of an ECG to that during normal exercise or activity to determine whether the change is significant and indicative of ischemia. Such monitoring systems are currently worn on the patient's waist or over the shoulders, and no active treatment is offered (since ischemia is only identified after the recording is complete, and the tape is scanned). It is possible that this information can be acquired in real time, such that appropriate drug therapy could be delivered to correct the ischemia. Closed loop intravenous drug delivery systems have been developed (and are undergoing evaluation) for the treatment of heart failure. Such systems could be incorporated into an inplantable device to permit the delivery of electrical therapy (pacing/cardioversion/defibrillation) as well as drug therapy, to correct a malfunctioning heart.

Despite these past efforts and the level of achievement prevalent among prior art systems, there are potential difficulties and drawbacks which may be experienced with such devices. The difficulties and drawbacks may be in large measure overcome or ameliorated by practicing the present invention, in both its system and method aspects, in which weighted multiparameter inputs are used to drive the system of the present invention.

SUMMARY OF THE INVENTION

The principle objects of the present invention are to provide a system for and method of treating a malfunctioning heart which provides for weighing at least two physiologic, such as hemodynamic, parameters (or functions thereof), measured against respective baselines, by summing the weighted parameters (or functions) to determine the presence of a malfunction and delivering output to the patient which may correct or overcome the malfunction.

Further objects of the present invention are to provide a system for and method of treating a malfunctioning heart which are responsive to change in at least two parameters, such as a pressure parameter, mixed venous $O_2$ and pH at one or more sites in the circulatory system of a patient and interior body or blood temperature of the patient.

Other objects of the present invention are to provide a system for and method of treating a malfunctioning heart which are responsive to change in at least two parameters, such as patient activity level, mixed venous $O_2$, interior body or blood temperature of a patient, and to an electrical signal, such as a R-wave-derived signal, or signals derived from the heart.

Yet further objects of the present invention are to provide a system for and method of treating a malfunctioning heart which are responsive to change in at least two parameters, such as patient activity level, mixed venous $O_2$ and pH at one or more sites in the circulatory system of a patient and interior body or blood temperature of the patient.

Yet other objects of the present invention are to provide a system for and method of treating a malfunctioning heart which are responsive to change in at least two parameters, such as patient activity level, mixed venous $O_2$, interior body or blood temperature of a patient, and to an electrical signal, such as a R-wave-derived signal, or signals derived from the heart.

Another object of the present invention is to provide an implantable system for treating a malfunctioning heart which achieves the above-stated objects.

From one vantage point, the present invention can be seen, in its apparatus aspect, as a system for treating a malfunctioning heart which includes means for supplying a plurality of a treatment modalities to a patient, means responsive to outputs of respective sensors of at least two parameters of a patient, at least one of which is a physiologic parameter. The system produces respective signal representation of the parameters or functions thereof. The respective signal representations or functions thereof are weighted. Processing means responsive to output from the means for weighing develop control output for selectively enabling the means for supplying a plurality of treatment modalities to the patient to effect selection of respective ones of treatment modalities as called for by the control output.

In its method aspect, the invention can be viewed as a method for treating a malfunctioning heart, which includes determining at least two parameters of a patient, at least one of which is a physiologic parameter, weighing the respective determined parameters or functions thereof and algebraically summing the weight parameters or functions thereof. The method also involves treating a patient with respective treatment modalities in accordance of the magnitude of the algebraic sum.

The foregoing objects of the present invention, in its system and method aspects, are achieved by the invention as defined in the appended claims.

DETAILED DESCRIPTION OF THE PREFERRED EMBODIMENTS

Figure 1:
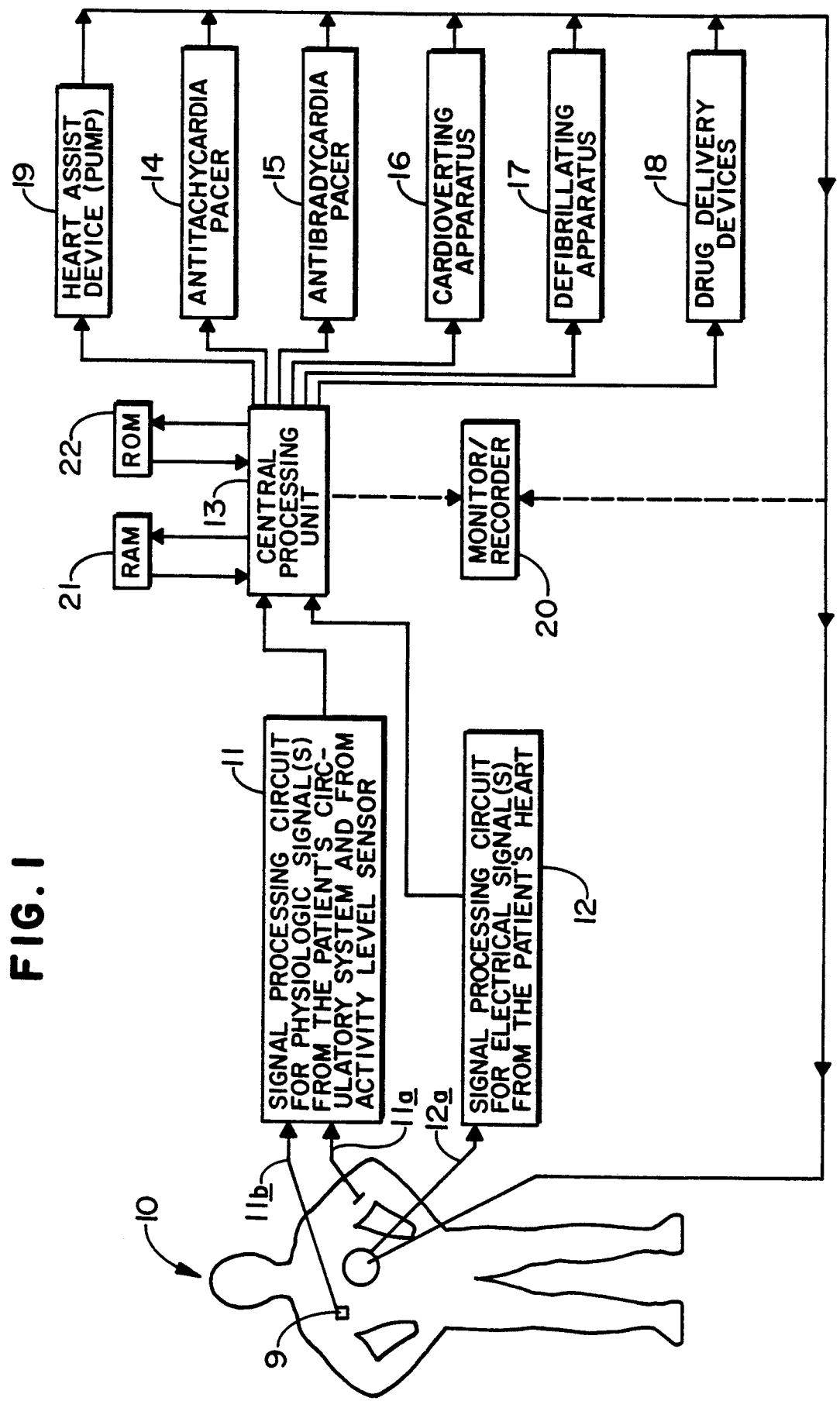
FIG. 1 is a block, generalized illustration of an exemplary, first embodiment of an electrical- and physiologic-signal responsive system for treating a malfunctioning heart in accordance with the present invention and for carrying out the invention in its method aspects.

As illustrated in FIG. 1, an exemplary system for treating a malfunctioning heart of a patient 10 includes a signal processing circuit 11 which receives signals, via a lead system shown graphically a line 11a, representing a physiologic condition or conditions at one or more sites within or related to the circulatory system of a patient. An activity level sensor, illustrated diagrammatically as an accelerometer 9, is carried in or on the patient 10. A signal representing the current activity level of the patient 10 is derived from output of the accelerometer 9 (or a similar motion sensor) and fed to the signal processing circuit 11 via the a lead 11b. The signal(s) representing the physiologic condition(s) preferably involve hemodynamic parameter(s) at the site(s) and reflect the dynamic nature of the pressure(s), $O_2$ saturation(s), pH(s) of blood, blood temperature(s) at the site(s) and/or interior body temperature(s). The system also includes a signal processing circuit 12 which receives an electrical signal or signals from the heart of a patient; for example, the circuit 12 may receive an electrical signal or signals, via the a lead system represented graphically by a line 12a obtained by conventional internal or external EKG electrodes and which are processed to derive a signal representing the QRS complex, the R-wave (the beating rate of the heart), a signal or signals related to atrial contractions (or the like) and/or a signal or signals related to ventricular contractions (or the like).

The signals from the signal processing circuits 11 and 12 are coupled to a central processing unit 13, which may be realized by a programmable microprocessor, with an associated ROM 22 and a RAM 21.

Preferably, the system illustrated in FIG. 1 includes a monitor/recorder 20, which may provide a visual and/or audible readout to aid medical personnel providing treatment for the patient. The monitor/recorder 20, as is known, may also effect recording, on strip graphs or the like, of the signals fed to the central processing unit 13, as well as the command signals from the central processing unit, which it generates in response to the processed signal(s) and the electrical signal(s) supplied thereto from the signal processing circuits 11 and 12.

The central processing unit 13 provides a number of output command signals, depending on decisions made by the central processing unit 13, under control of its associated RAM 21 and ROM 22. Of course, the central processing unit 13 may elect, without producing any output command signals, to continue monitoring the signal(s) and the signal(s) from the signal processing circuits 11 and 12, in the event neither malfunction of the heart of the patient 10 nor patient compromise has been identified.

The signal(s) from the signal processing circuits 11 and 12 may be processed by the central processing unit 13 to derive varying, long-term baseline(s) for the physiologic parameter(s) against which current, short-term magnitude(s) of the physiologic parameter(s) is (are) to be compared. In another embodiment, the programmable central processing unit 13, in conjunction with its associated RAM 21 and ROM 22, may develop a fixed baseline or baselines, which is or are adjustable and against which the selected physiologic parameter or parameters may be compared.

In the event a malfunction of the heart of the patient 10 is identified by the central processing unit 13, the central processing unit supplies an enabling command signal or signals, depending on the nature of the identified malfunction, to one or another or more than one malfunction correcting means, illustrated as an antitachycardia pacer 14, an antibradycardia pacer 15, a cardioverting apparatus 16, a defibrillating apparatus 17, drug delivery devices 18, and a heart-assist device 19, which may be an assist pump or a similar device. It is to be appreciated that cardioverter and defibrillator may share components and be constructed as illustrated in U.S. Pat. No. 4,774,950.

The malfunction correcting circuits 14–17 produce respective malfunction correcting electrical output signals, which are delivered to the patient 10 as required. The drug delivery devices 18 which may consist of a number of pumps or other drug delivery devices, such as gravity operated delivery systems supply medications to the patient 10 in an effort to overcome or correct the malfunction. The heart-assist device 19, which may be a pump, when energized aids a patient by assisting pumping action thereby reducing load on the heart or drugs which are supplied to the patient 10 in an effort to overcome the malfunction. These output signals and/or drug(s) and/or the pumping assist are provided to effect termination of, or at least treat in an effective manner, singly or in combination stable SVT, unstable SVT, stable VT, unstable VT, stable atrial fibrillation, unstable atrial fibrillation, ventricular fibrillation, asystole, stable bradycardia, unstable bradycardia, ischemia, early infarction and both stable and unstable heart failure.

Figure 2:
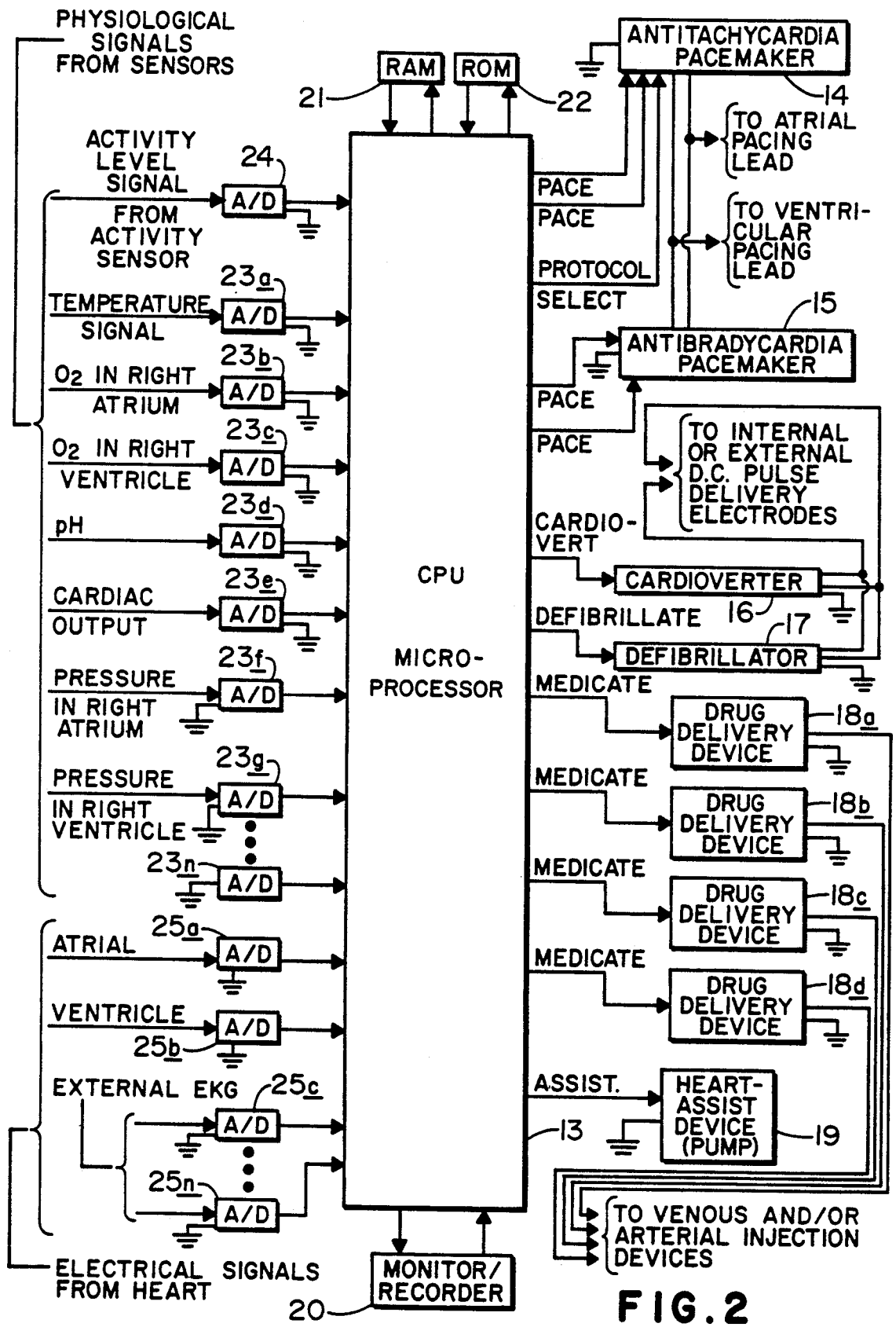
FIG. 2 is a more detailed illustration of the exemplary system shown in FIG. 1 for treating a malfunctioning heart and for carrying out the invention in its method aspects.

As illustrated in FIG. 2, the first preferred detailed embodiment, like the more generalized illustration thereof shown in FIG. 1, is provided with a CPU 13 and its associated RAM 21 and ROM 22. If desired inputs and outputs to and from the CPU 13 may be fed to a monitor/recorder 20.

The input side of the system, includes a plurality of physiologic signals, actually electric analogue signal representations of physiologic conditions, shown by way of example as interior body temperature, $O_2$ level of mixed venous blood in right atrium, $O_2$ level of mixed venous blood in right ventricle, pH of blood, cardiac output, pressure in the right atrium of the heart of the patient and pressure in the right ventricle of the heart of the patient. Other possible signals could represent $CO_2$ level in blood, end tidal $CO_2$ level in blood, DP/dt, blood temperature, respiratory rate and lactic acidosis, to name a few. The respective physiologic signals are converted into digital signals by respective analogue-to-digital converters 23a to 23n and supplied as distinct converted inputs to the CPU 13. Additionally, a patient activity level signal, which may be from an accelerometer (9, FIG. 1) or other motion sensor carried by the patient, is fed to an analogue-to-digital converter 24, and, as converted fed another input to the CPU 13.

The system of FIG. 2 includes electrical signals derived from action of the patient's heart. The electrical signals, as illustrated, include an atrial EKG signal, a ventricular EKG signal and a plurality of external EKG signals, which are obtained by conventional means. The respective electrical signals are fed to respective analogue-to-digital converters 25a–25n and are converted into respective digital signals which are fed, as distinct inputs, to the CPU 13.

The CPU 13 effects a comparison of one or more of the digital signal representations of the physiologic signals from the analogue-to-digital converters 23a–23n against a respective fixed (for example, as disclosed in U.S. Pat. No. 4,967,749) or a respective varying baseline (for example, as disclosed in U.S. Pat. No. 4,774,950) representations thereof, possible after processing the signals into signals representing mean, systolic, diastolic, pulse pressures or the like. Especially useful in practicing the present invention are the right ventricular pulse pressure (RVPP), the right ventricular systolic pressure (RVSP) and the right atrial pressure (RAP). Arterial blood pressure also may be a particularly useful parameter. Similarly, mixed venous $O_2$ saturation (MVO$_2$) in the right atrium and/or in the right ventricle of the heart and/or elsewhere in the central venous system are useful parameters. Temperature of the interior of the patient's body also may be determined and compared against a fixed or long-term varying baseline. The CPU 13 also determines the current heart rate from one of the electrical signals from the analogue-to-digital converters 25a–25n and the activity level of the patient from the input provided from the analogue-to-digital converter 24.

Figure 6A:
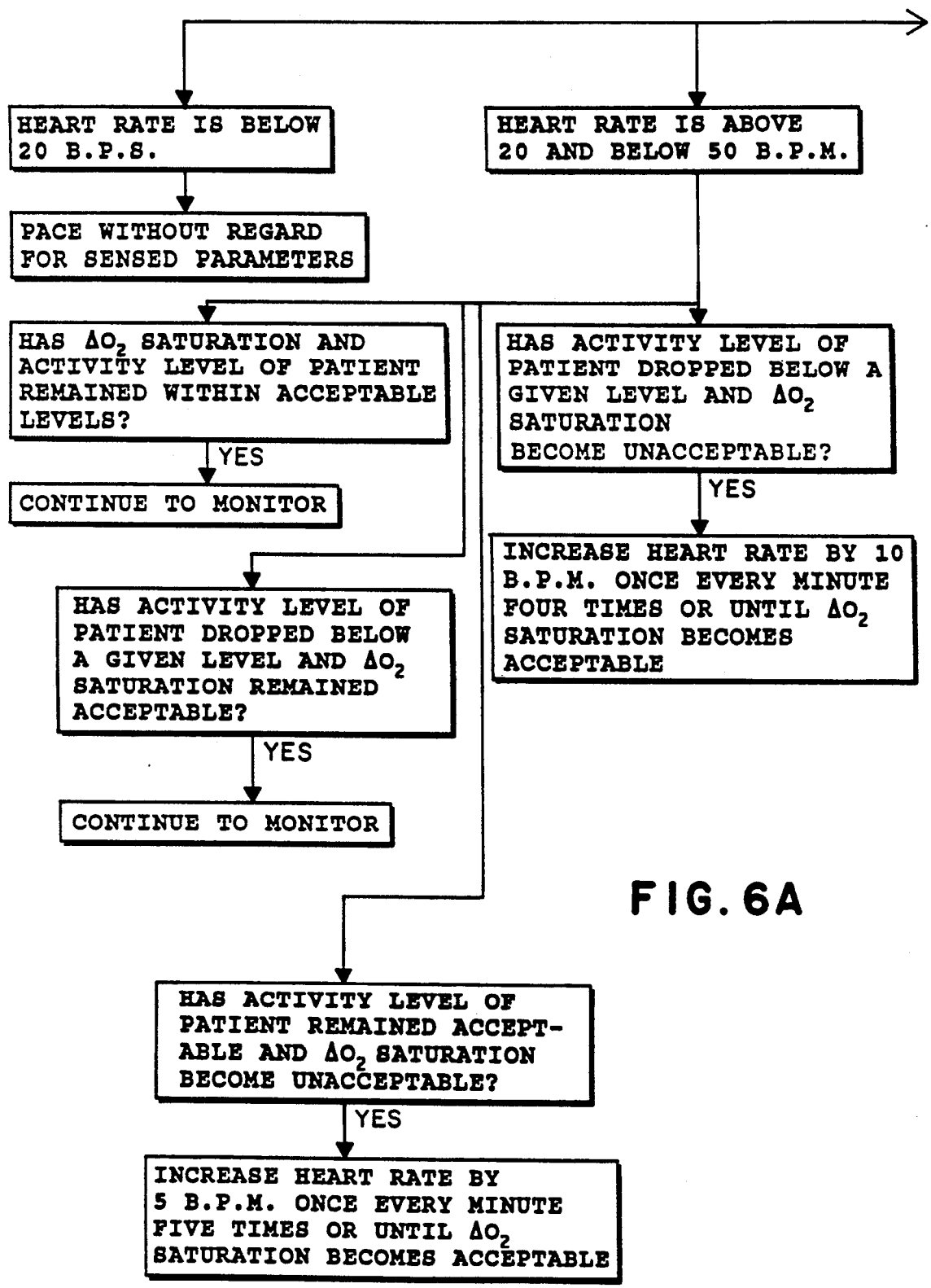
FIGS. 6A-6C, when taken together, constitute a flow chart of a first set of exemplary routines which may be executed by the systems illustrated in FIGS. 1, 2 and 3, 4.
Figure 6B:
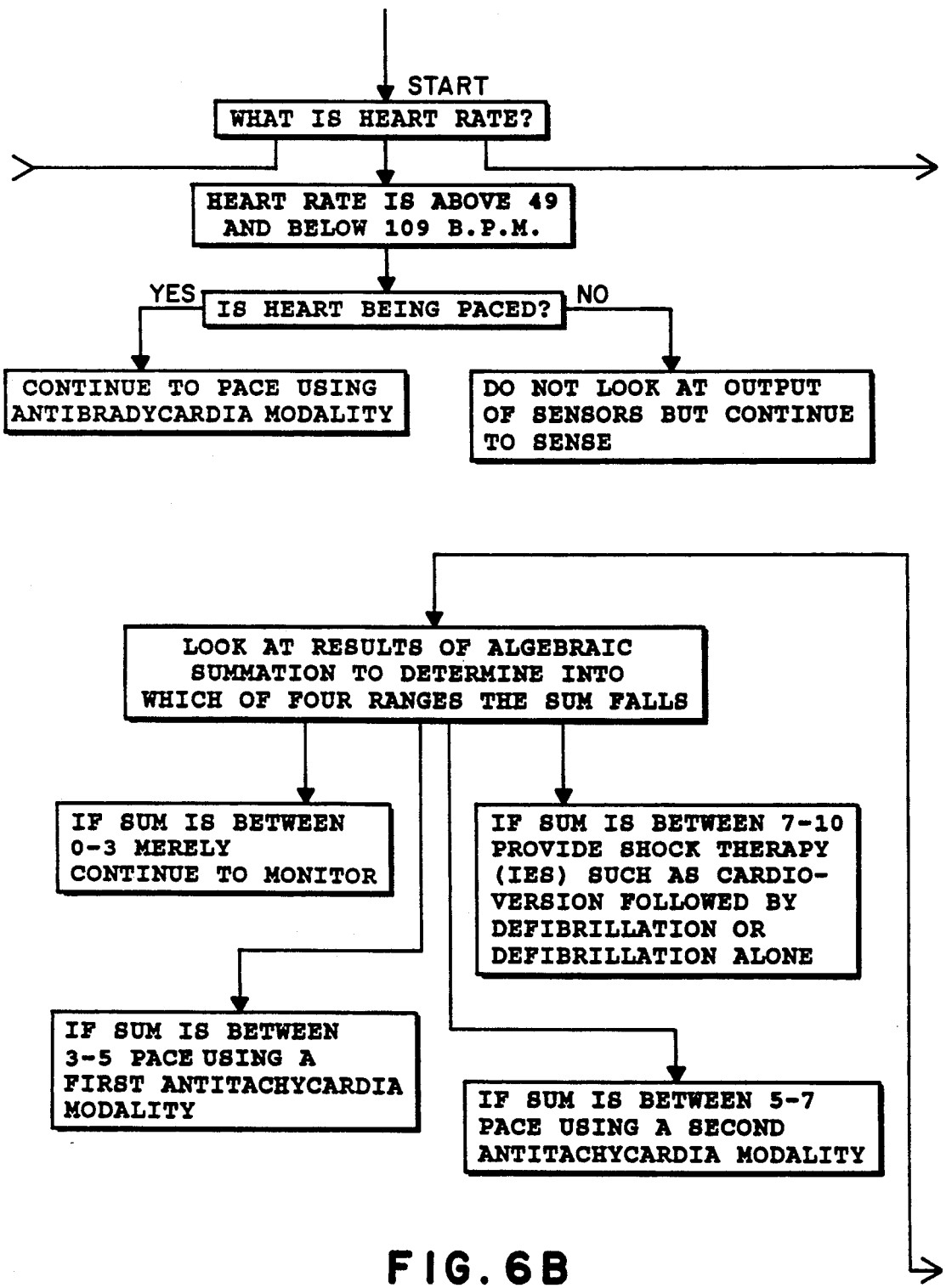
Figure 6C:
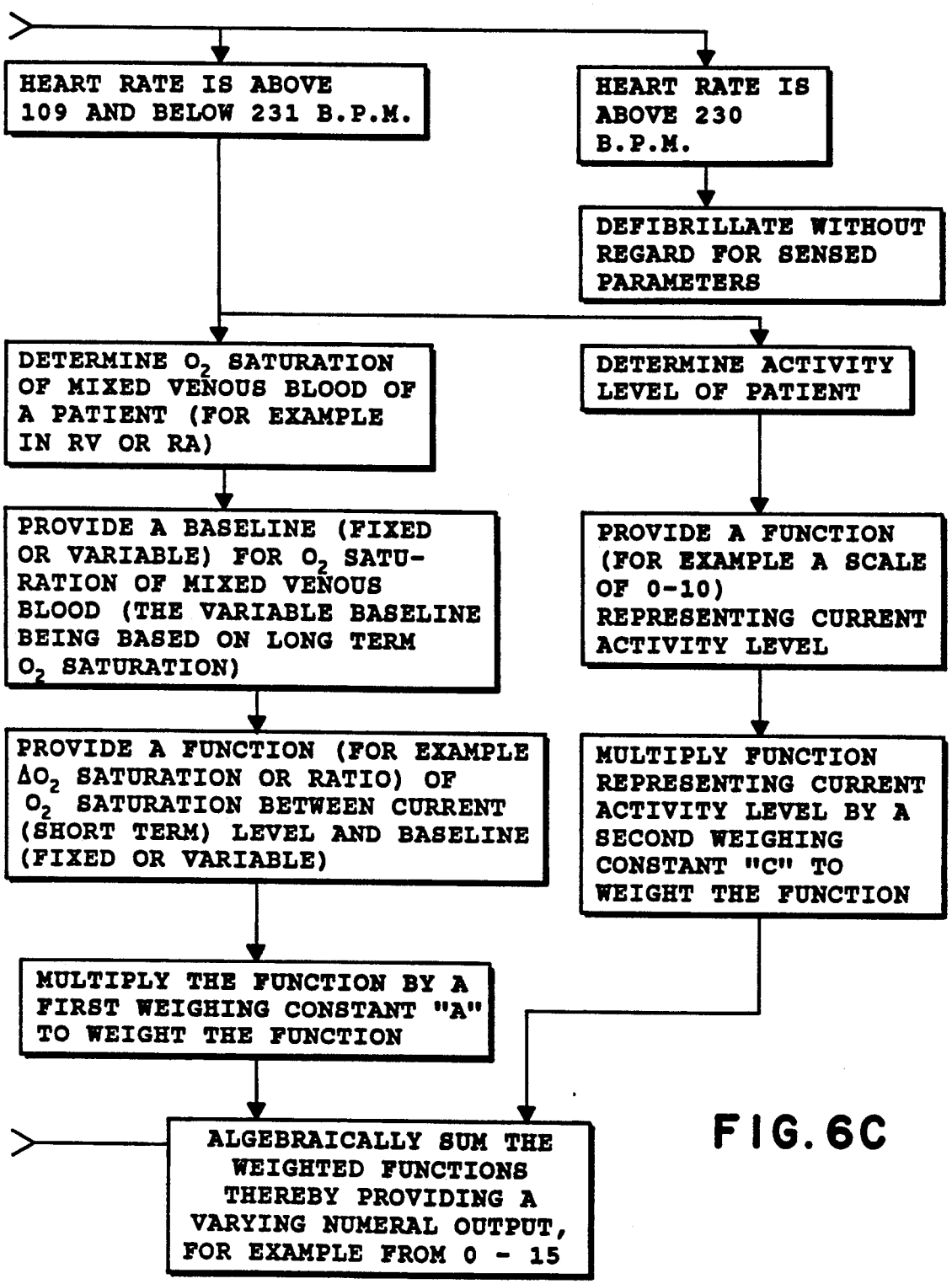
Figure 7:
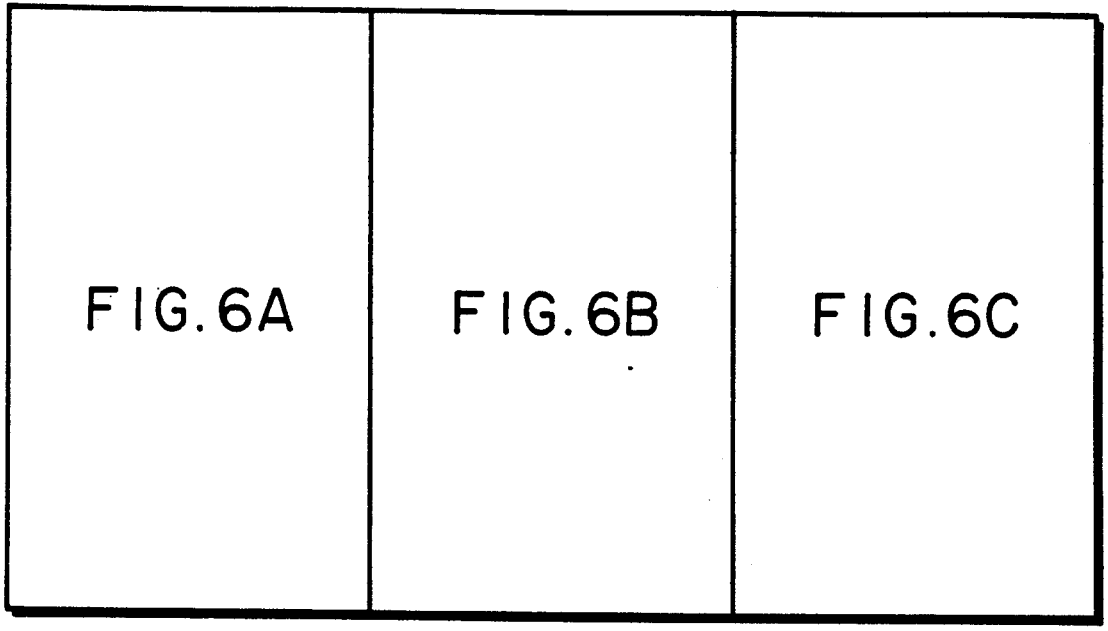
FIG. 7 is a diagrammatic showing of the placement of FIGS. 6A-6C so that one may view these figures as a whole.
Figure 9:
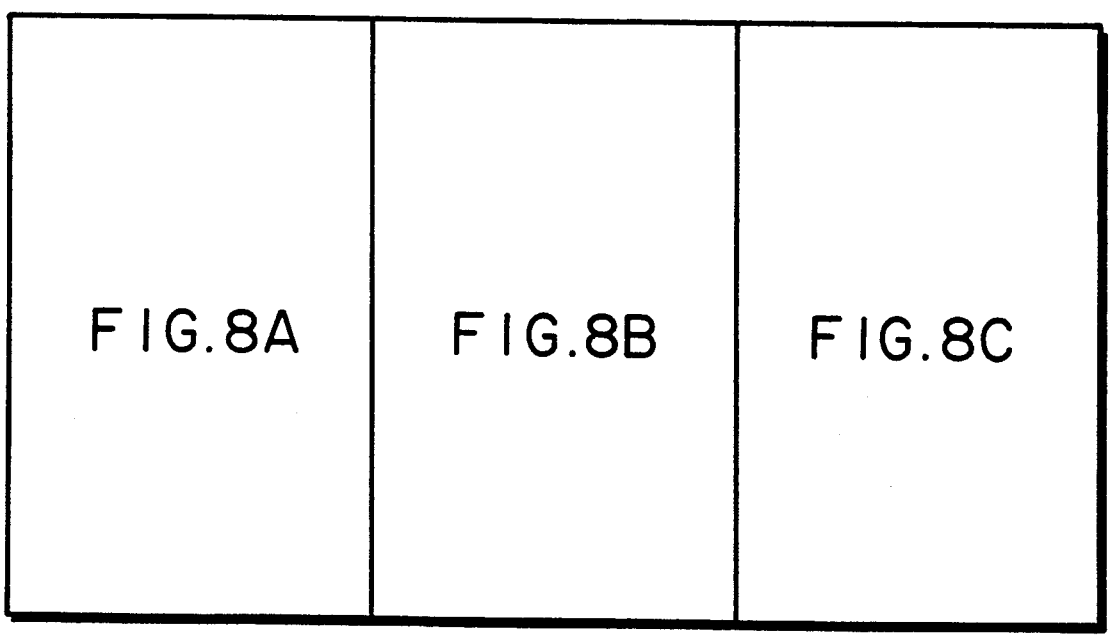
FIG. 9 is a diagrammatic showing of the placement of FIGS. 8A-8C in order so that one may view these figures as a whole.
Figure 8A:
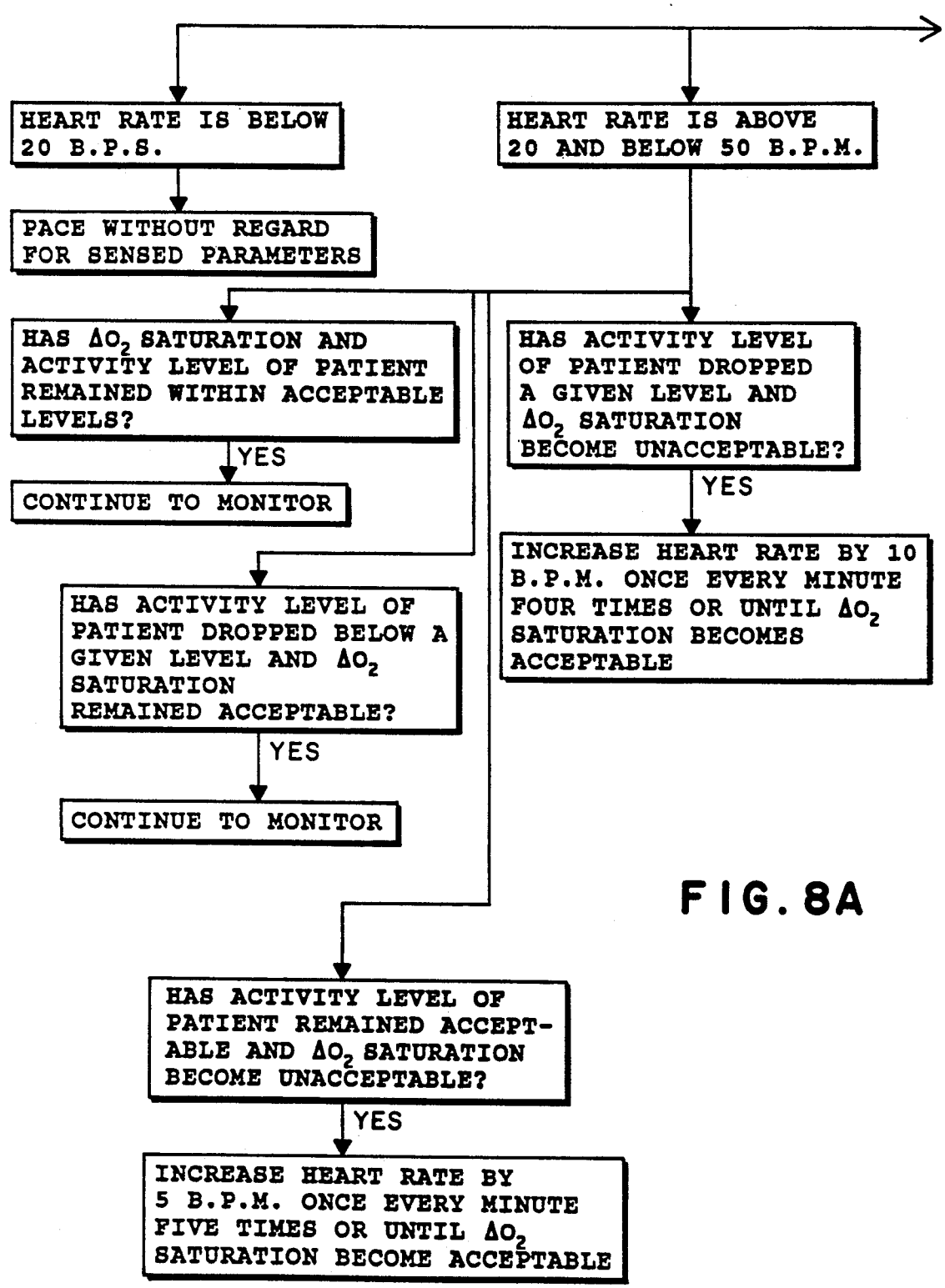
FIG. 8A-8C, when taken together, constitute a flow chart of a second set of exemplary routines which may be executed by the systems illustrated in FIGS. 1, 2 and 3, 4.
Figure 8B:
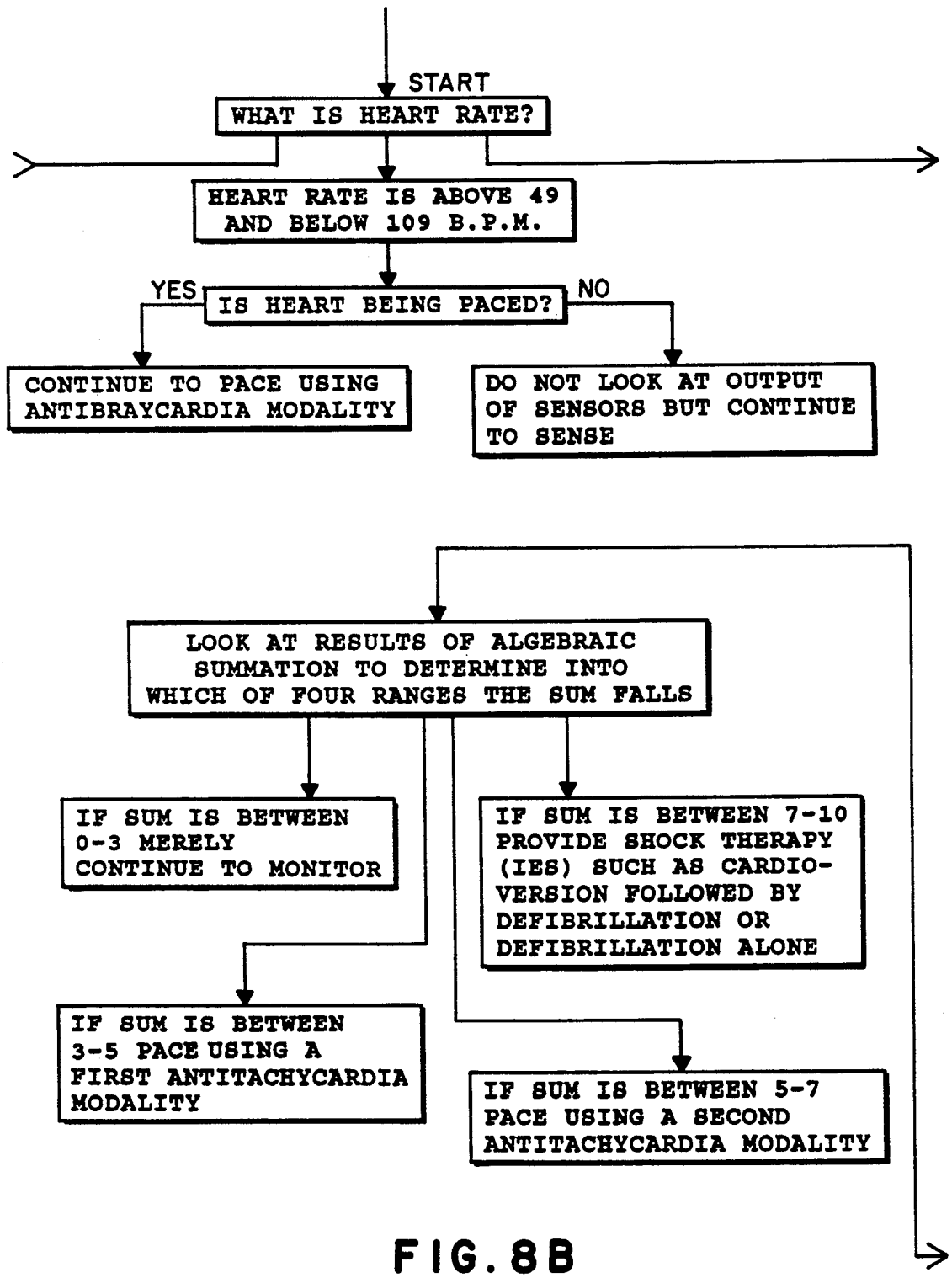
Figure 8C:
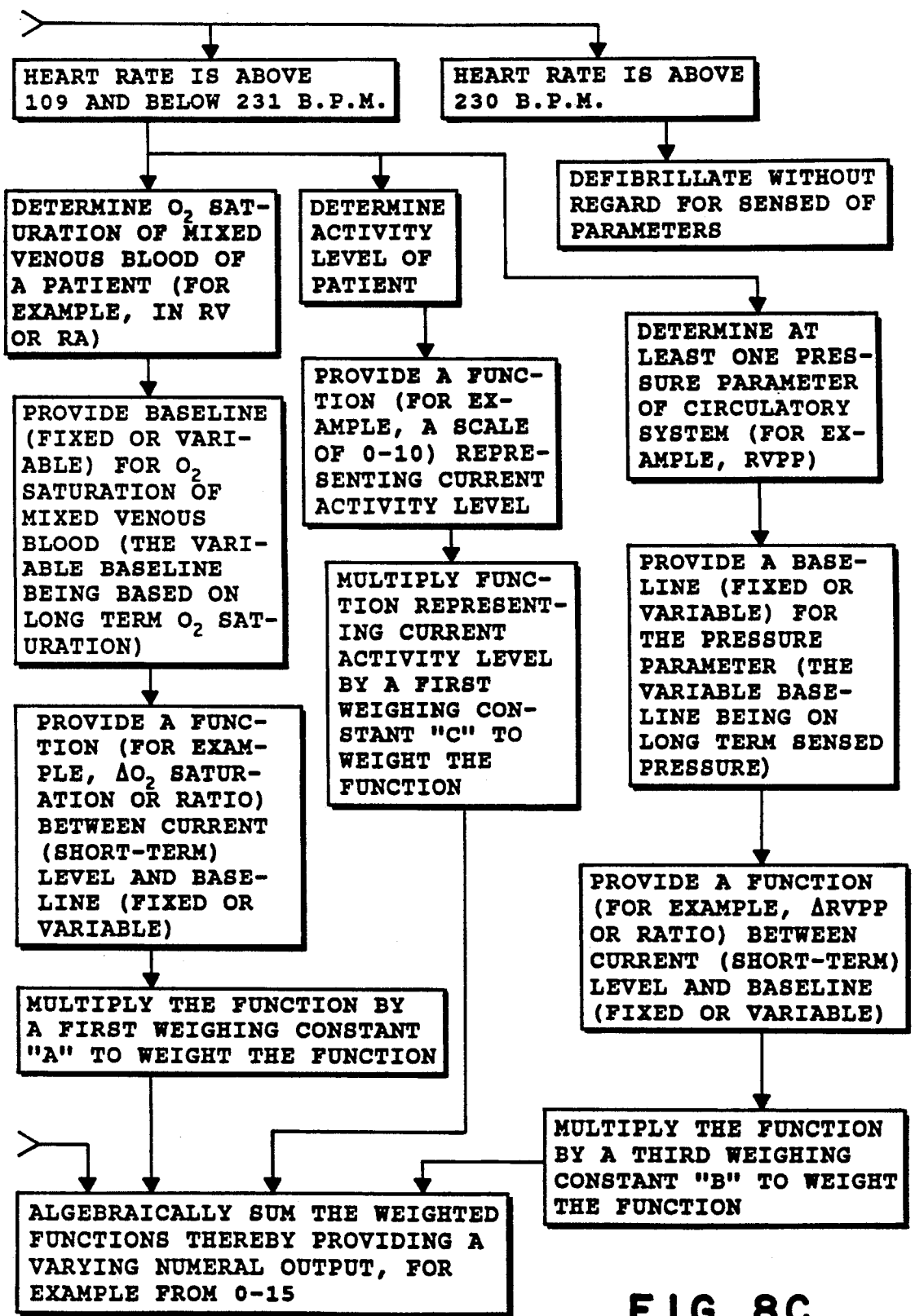

The CPU 13, using programs stored in the ROM 21, may determine if any of the malfunctions set out in FIGS. 6A–6C is present and produces control signals which are fed respectively to the antitachycardia pacemaker 14, to the antibradycardia pacemaker 15, to the cardioverter 16, to the defibrillator 17, to the respective drug delivery devices 18a-18d and to the heart-assist device (pump) 19. Each of the pacemakers 14 and 15 receive two possible pacing command signals from the CPU 13, one to effect production of an atrial pacing and the other to effect ventricular pacing. Thus, single or dual chamber pacing is possible when an effort is under way to treat tachycardia or bradycardia. Moreover, a protocol select signal from the CPU 13 enables the antitachycardia pacemaker 14 to function in at least two different modes to supply differing pacing protocols, one more aggressive than the other, depending on the severity of the malfunction. The diagnostic and treatment routines which are carried out by the central processing unit 13, with its associated RAM 21 and ROM 22 in accordance with the present invention, are set out in FIGS. 6A-6C and, in a differing version, as set out in FIGS. 8A-8C.

Figure 3:
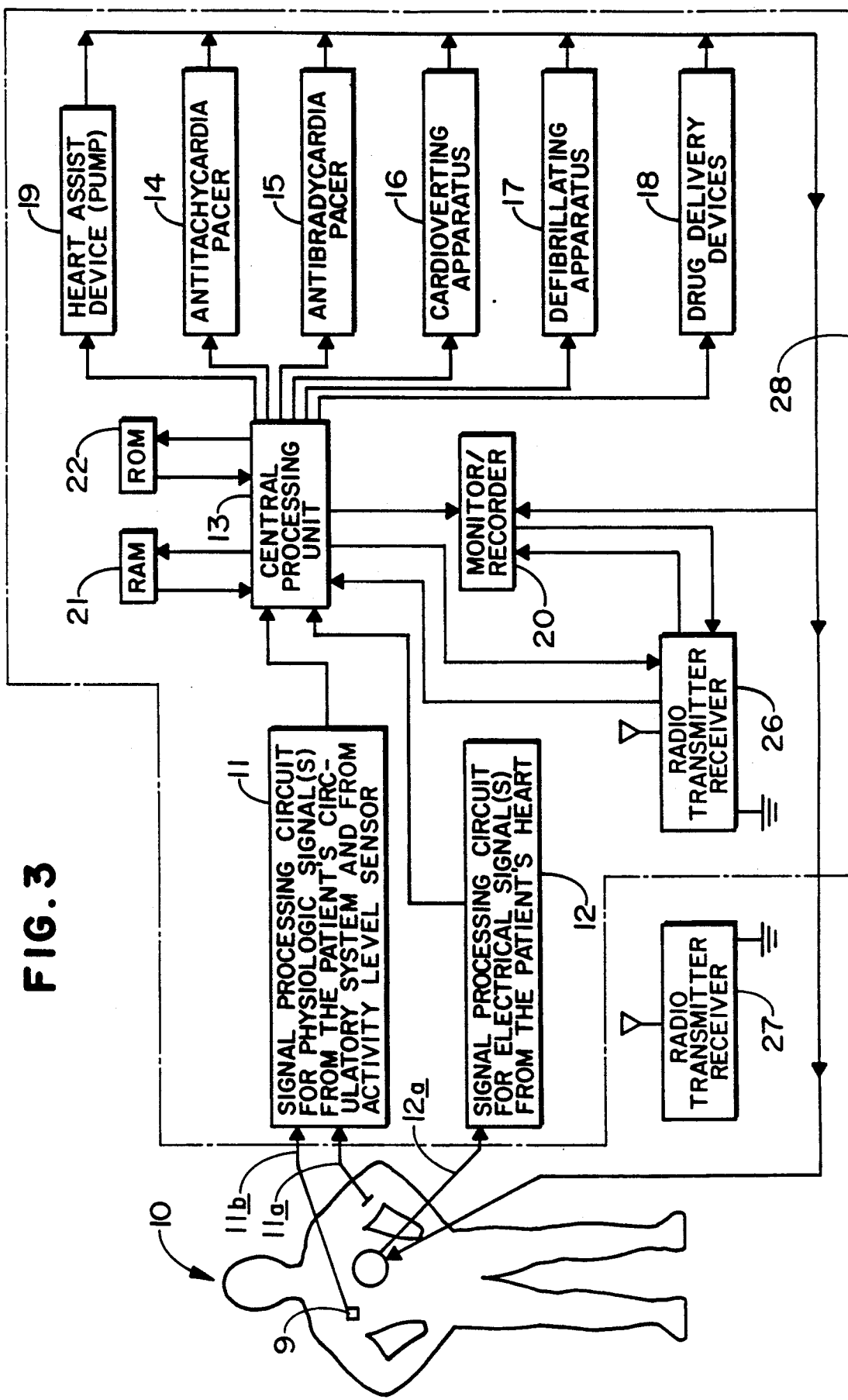
FIG. 3 is a block, generalized illustration of an exemplary, second embodiment of an electrical- and physiologic-signal responsive system for treating a malfunctioning heart in accordance with the present invention and for carrying out the invention in its method aspects.

As illustrated in FIG. 3, an exemplary system for treating a malfunctioning heart of a patient 10 includes an implantable portion 28. The implantable portion 28 comprises a signal processing circuit 11 which receives signals, via a lead system shown graphically as a line 11a representing a physiologic condition or conditions at one or more sites within or related to the circulatory system of a patient. An activity level sensor, illustrated diagrammatically as an accelerometer 9, is carried in or on the patient 10. A signal representing the current activity level of the patient 10 is derived from output of the accelerometer 9 (or a similar motion sensor) and fed to the signal processing circuit 11 via a lead 11b. The signal(s) representing the physiologic condition(s) preferably involve hemodynamic parameter(s) at the site(s) and reflect the dynamic nature of the pressure(s), $O_2$ saturations(s), pH(s) of blood, blood temperature(s) at the site(s) and/or interior body temperature. The system also includes a signal processing circuit 12 which receives an EKG electrical signal or EKG signals from the heart of a patient; for example, the circuit 12 may receive an electrical signal or signals via a lead system, represented graphically by line 12a obtained by conventional internal or external EKG electrodes and which are processed to derive a signal representing the QRS complex, the R-wave (the beating rate of the heart), a signal or signals related to atrial contractions (or the like) and/or a signal or signals related to ventricular contractions (or the like).

The signals from the signal processing circuits 11 and 12 are coupled to a central processing unit 13, which may be realized by a programmable microprocessor, with an associated a ROM 22 and a RAM 21.

Preferably, the system illustrated in FIG. 3 includes a monitor/recorder 20, which is coupled with a radio transmitter-receiver 26 and which, upon a command signal from the receiver portion of the transmitter-receiver 27, will respond to commands and feed to the transmitter portion of the transmitter-receiver 26 signals representing stored signals fed to the central processing unit 13, as well as the command signals from the central processing unit, which it generates in response to the physiologic signal(s) and the electrical signal(s) supplied thereto, and signals representing the presence or absence of output from the respective devices 14-19. The implanted radio transmitter-receiver 26 is coupled to a radio transmitter-receiver 27, the transmitter portion of which provides command signals to the radio transmitter 26 to effect recall of data stored in the monitor/recorder 20. The transmitter-receiver 26 and the transmitter-receiver 27 may be used to effect a reprogramming of the CPU 13 with its associated RAM 21 and ROM 22, if desired to change or to set the baselines, therapy delivery routines, set points and the like. Of course, magnetic or ultrasonic links could be used instead of the radio link. It is to be understood that in some practical realization of the system the monitor/recorder 20 functions could be carried out by dedicated portions of the RAM 21 and ROM 22 or a special storage member in or associated with the central processing unit 13.

The central processing unit 13 provides a number of output command signals, depending on decisions made by the central processing unit 13, under control of its associated RAM 21 and ROM 22. Of course, the central processing unit 13 may elect, without producing any output command signals, to continue monitoring the electrical signal(s) and the physiologic signal(s) from the signal processing circuits 11 and 12, in the event no malfunction of the heart of the patient 10 has been identified.

The signal(s) from the signal processing circuit 13 may be processed by the central processing unit 13 to derive varying, long-term baseline(s) for the physiologic parameter(s) against which current, short-term magnitude(s) of the physiologic parameter(s) is (are) to be compared. In another embodiment, the programmable central processing unit 13, in conjunction with its associated RAM 21 and ROM 22, may develop a fixed baseline or baselines, which is or are adjustable and against which the selected physiologic parameter or parameters may be compared.

In the event a malfunction of the heart of the patient 10 is identified by the implanted central processing unit 13, the central processing unit supplies an enabling command signal or signals, depending on the nature of the identified malfunction, to one or another or more than one malfunction correcting means, illustrated as an antitachycardia pacer 14, an antibradycardia pacer 15, a cardioverting apparatus 16, a defibrillating apparatus 17 drug delivery devices 18, and a heart-assist device 19, which may be an assist pump or a similar device. It is to be appreciated that cardioverter and defibrillator may share components and be constructed as illustrated in U.S. Pat. No. 4,774,950.

The malfunction correcting circuits 14-17 produce respective malfunction correcting electrical output signals, which are delivered to the patient 10 as required. The drug delivery devices 19 which may consist of a number of pumps or other drug delivery devices, such as gravity operated delivery systems supply medications to the patient 10 in an effort to overcome or correct the malfunction. The heart-assist device 19, which may be a pump, when energized, aids a patient by assisting pumping action thereby reducing load on the heart or drugs which are supplied to the patient 10 in an effort to overcome the malfunction. These output signals and/or drug(s) and/or the pumping assist are provided to effect termination of, or at least treat in an effective manner, singly or in combination stable SVT, unstable SVT, stable VT, unstable VT, stable atrial fibrillation, unstable atrial fibrillation, ventricular fibrillation, asystole, stable bradycardia, unstable bradycardia, ischemia, early infarction and both stable and unstable heart failure.

Figure 4:
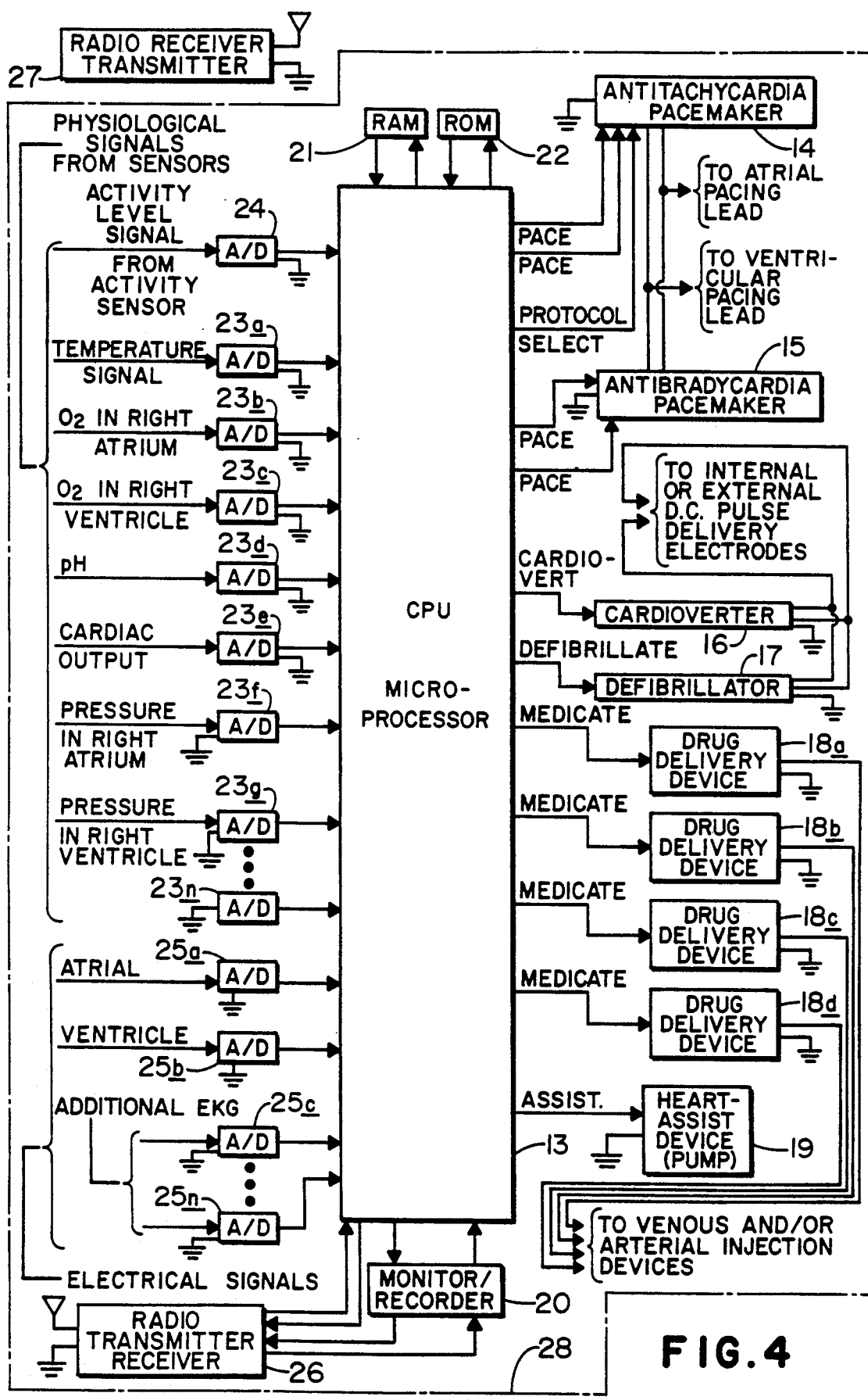
FIG. 4 is a more detailed illustration of the exemplary system shown in FIG. 3 for treating a malfunctioning heart in accordance with the present invention and for carrying out the invention in its method aspects.

As illustrated in FIG. 4, the second preferred detailed embodiment, like the more generalized illustration thereof shown in FIG. 3, is provided with a CPU 13 and its associated RAM 21 and ROM 22. If desired inputs and outputs to and from the CPU 13 may be fed to a monitor/recorder 20 which monitors and stores data, as in the detailed system shown in FIG. 3. The monitor/recorder 20 may also, as in the system of FIG. 3, effect a monitoring of the condition of the devices 14-19 and a history of actions effected.

The input side of the system, includes a plurality of physiologic signals, actually electric analogue signal representations of physiologic conditions, shown by way of example as interior body temperature, $O_2$ level of mixed venous blood in right atrium, $O_2$ level of mixed venous in right ventricle, pH of blood, cardiac output, pressure in the right atrium of the heart of the patient and pressure in the right ventricle of the heart of the patient. Other possible signals could represent $CO_2$ level in blood, end tidal $CO_2$ level in blood, DP/dt, blood temperature, respiratory rate and lactic acidosis, to name a few. The respective physiologic signals are converted into digital signals by respective analogue-to-digital converters $23a$ to $23n$ and supplied as distinct inputs to the CPU 13.

The system of FIG. 4 includes electrical signals derived from action of the patient's heart. The electrical signals, as illustrated, include a right atrial signal, a right ventricular signal and a plurality of external EKG signals, which are obtained by conventional means. The respective electrical signals are fed to respective analogue-to-digital converters $25a-25n$ and are converted into respective digital signals which are fed, as distinct inputs, to the CPU 13.

The CPU 13 effects a comparison of one or more of the digital signal representations of the physiologic signals from the analogue-to-digital converters $23a-23n$ against a respective fixed (for example, as disclosed in U.S. Pat. No. 4,967,749) or a respective varying baseline (for example, as disclosed in U.S. Pat. No. 4,774,950) representations thereof, possibly after processing the signals into signals representing mean, systolic, diastolic, pulse pressures or the like. Especially useful in practicing the present invention are the right ventricular pulse pressure (RVPP), the right ventricular systolic pressure (RVSP) and the right atrium pressure (RAP). Similarly, mixed venous $O_2$ saturation ($MVO_2$) in the right atrium and/or in the right ventricle of the heart and/or elsewhere in the central venous system. Temperature of the interior of the patient's body also may be determined and compared against a fixed or long-term varying baseline. The CPU 13 also determines the current heart rate from one of the electrical signals form the analogue-to-digital converters $25a-25n$ and the activity level of the patient from the input provided from the analogue-to-digital converter 24.

The CPU 13, using programs stored in the ROM 21, may determine if any of the malfunctions set out in FIGS. 6A-6C is present and produces control signals which are fed respectively to the antitachycardia pacemaker 14, to the antibradycardia pacemaker 15, to the cardioverter 16, to the defibrillator 17, to the respective drug delivery devices $18a-18d$ and to the heart-assist device (pump) 19. Each of the pacemakers 14 and 15 receive two possible pacing command signals from the CPU 13, one to effect production of an atrial pacing and the other to effect ventricular pacing. Thus, single or dual chamber pacing is possible when an effort is under way to treat tachycardia or bradycardia. Moreover, a protocol select signal from the CPU 13 enables the antitachycardia pacemaker 14 to function in at least two different modes to supply differing pacing protocols, one more aggressive than the other, depending on the severity of the malfunction. The diagnostic and treatment routines which are carried out by the central processing unit 13, with its associated RAM 21 and ROM 22 in accordance with the present invention, are set out in FIGS. 6A-6C and, in a differing version, as set out in FIGS. 8A-8C.

The pair of radio transmitter-receivers 26 and 27, as in the system shown in FIG. 3, provide a wireless link from the implantable portions of the system to a station outside the patient. The link not only allows one to retrieve data from the monitor/recorder 20, but also allows one to reprogram the CPU 13 and its associated RAM 21 and ROM 22 to effect resetting of the baselines, durations of the given (long term) baseline periods, duration of the predetermined (short term) baseline periods and the patient treatment routines.

It is to be appreciated that the programmable microprocessor 13 (FIGS. 1-4), with its associated RAM 21 (FIGS. 1-4) and ROM 22 (FIGS. 1-4), is effective to carry out the method of the present invention. The digital signal representations of the parameters or functions thereof (such as ratios or differences between long term and short term magnitudes of the respective parameters or short term magnitudes of the respective parameters determined against respective adjustable fixed baselines) are respectively weighted using a mathematical expression which may be generalized as follows:

$$A \cdot f(x) + B \cdot f(y) + C \cdot f(i) = Z \qquad (1)$$

where "x" is a first physiologic parameter, "y" is a second physiologic parameter and "i" is activity level of the patient or a third physiologic parameter. "A", "B" and "C" are respective weighing constants. "Z" is the algebraic sum. The algebraic sum "Z" represents the condition of the patient, from a physiologic and/or hemodynamic perspective, as reflected by the weighted parameters. The greater the magnitude of Z, the more aggressive the treatment modality selected. For example, if Z is below 3, the system merely continues to monitor and to evaluate the selected parameters without applying any antitachycardia treatment to the patient. If Z is between 3 and 5 antitachycardia pacing of a first modality occurs. If Z is between 5 and 7 antitachycardia pacing of a second modality occurs, the second modality being more aggressive than the first. If Z is between 7 and 10 defibrillation therapy occurs, or a more complex shock therapy occurs, such as low energy cardioversion therapy, followed by higher energy cardioversion therapy and, if necessary, defibrillation therapy.

The system may be so programmed that the numerical variation of Z is exponential, rather than linear. The system also may be programmed to limit the above-noted treatment modalities to particular heart-rate ranges. A maximum heart rate cut off could be provided above which defibrillation is attempted without regard to the weighted parameters. The system and method also could be operatively associated with provisions for treating bradycardia, again directed by a particular minimum heart rate and/or low heart rate range(s).

The above-noted generalized formula (1) may be modified so that only two parameters are involved by simply making one of the constants A, B, C zero. More than three parameters may be used, by adding more terms to the generalized formula (1) and selecting a new series of constants.

As a more specific example, once a too high heart rate has been identified, two physiologic parameters and activity level of a patent are considered, in accordance with a formula expressed as follows:

$$A(\Delta RVPP) + B(\Delta O_2 \text{ Saturation}) + C(\text{Activity Level}) = Z \quad (2)$$

Weighing constant A is 1; weighing constant B is 2; and weighing factor C is $-2$. $\Delta$RVPP is the difference between current (short term, for example, as determined over six seconds), right ventricular pulse pressure and a baseline therefor (fixed or long term, for example, as determined over 60 seconds). $\Delta O_2$ saturation is the difference between current (short term) $O_2$ saturation of mixed venous blood in the right ventricle or right atrium and long term $O_2$ saturation of mixed venous blood in the right ventricle or right atrium. (Activity Level) is a measure of intensity of movement of a patient on a scale of 0 to 10, for example, 0 indicating no movement and 10 indicating a high level of movement, such as one would have when running.

Instead of RVPP, it is contemplated that RVSP and RAP could be used to advantage in place of RVPP were pressure to be one of the selected physiologic parameters. Temperature of an interior portion of the body of a patient or pH of the blood or temperature of the blood, particularly in an interior portion of the body could be used as well.

Instead of selecting differences between current (short term) and baseline (fixed or varying long term) levels for the parameters, we could select functions which involved ratios rather than differences. Of course, the respective weighing constants "A", "B" and "C" would differ. In this case A could be 2; B could be 1 and C could be $-1$.

It is to be understood that other formulae could be used in practicing the present invention, including more complex ones. Among the simpler ones are equations which take into account two parameters reflecting patient condition. One of these, taking into account mixed venous $O_2$ saturation and activity level of the patient, could be expressed as follows:

$$A \cdot f(x) + C \cdot f(i) = Z \quad (3)$$

where x and i are respectively functions of (1) mixed venous $O_2$ saturation in the right ventricle (RV) or right atrium (RA) and (2) activity level of the patient expressed on a scale of 0–10. Interior (central) body temperature or blood temperature in an interior portion of the circulatory system of a patient could be used in place of the activity level of a patient, making appropriate changes in the weighing constants. Were one to use pH as one of the two parameters one could substitute pH for $O_2$ saturation. Were one to use a pressure parameter, as a substitute for $O_2$ saturation, RVPP could be advantageously used. As in the three-parameter cases, the function(s) of the respective current (short term) parameters to be weighted could be ratio(s) or difference(s) ($\Delta$) between the current parameter(s) and baseline(s), fixed or varying. The varying baseline(s) reflecting the long term parameter(s) measured over periods longer than used to acquire the short term so called current valves.

When integrating the invention with an antibradycardia treatment system, it is to be understood that looking at the differences (or ratios) of at least one of the parameters, could be used to effect changes in pacing rate (or escape interval) of an antibradycardia pacemaker driven by the function of a selected one or another or a plurality of the parameters. For example, at heart rates below 50 b.p.m., the function $\Delta O_2$ saturation and function of activity level measured on a scale of 0–10 could be used to change the paced heart rate to assure that the $O_2$ saturation is appropriate.

Figure 5:
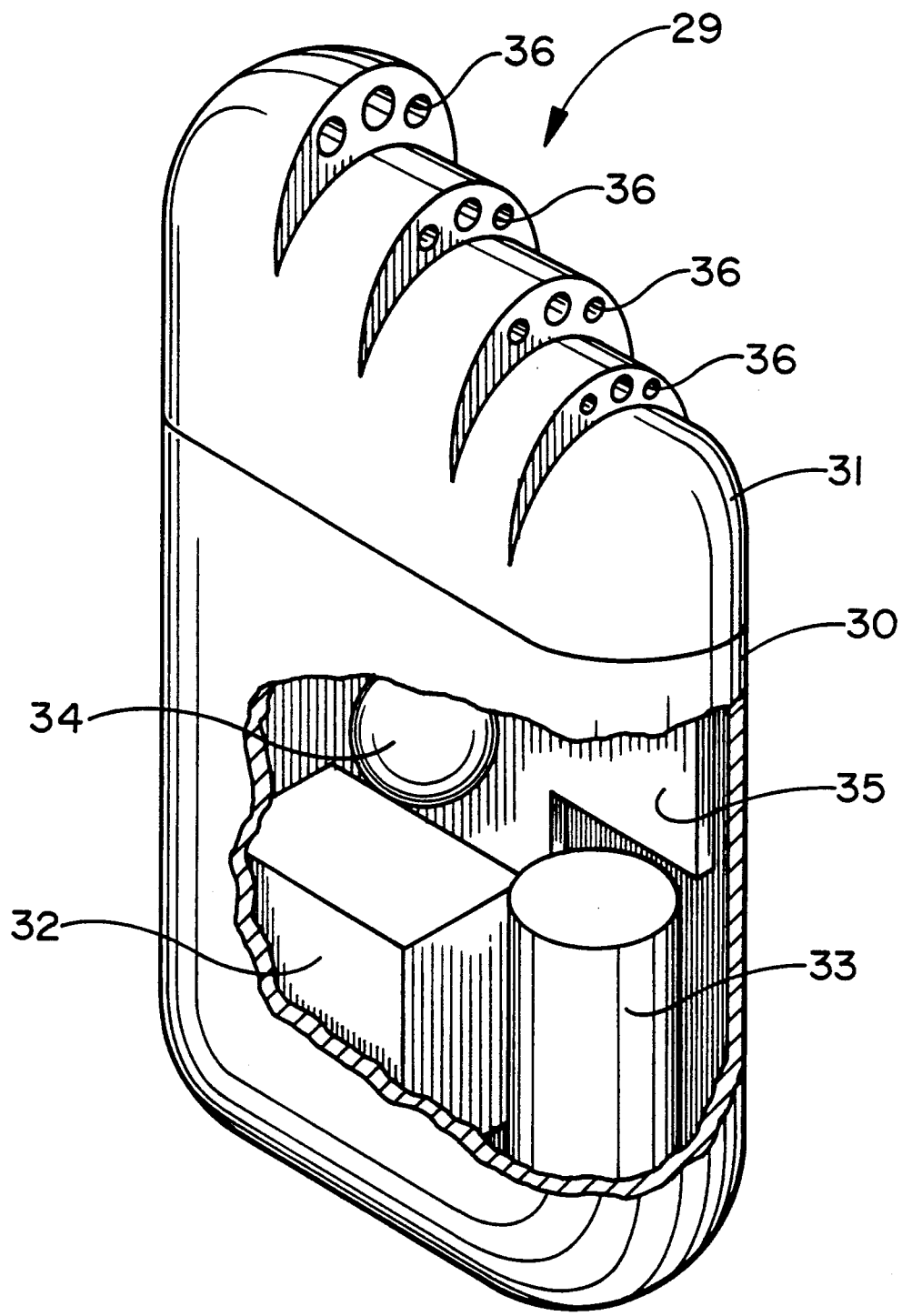
FIG. 5 is a pictorial illustration of an exemplary implantable controlled electrical energy pulse generator which may be used as a component of an implantable system shown in FIGS. 3 and 4, for treating a malfunctioning heart in accordance with the present invention, the housing of the generator being partially broken away to show positioning of major components thereof.

One possible general implantable configuration of a housing 29, which may be used in practicing the present invention, is shown in FIG. 5. The housing 29 includes a case 30, made of titanium, and a header 31, formed of an epoxy material, fixed to the case 30, all external components being hermetically sealed and biocompatible for human implantation. Within the case 30 are an accelerometer, a battery pack or battery 32, at least one energy storage capacitor 33, an accelerometer 34, an electronic module 35 in or on which circuit components, other than the accelerometer 34, the battery pack or battery 32 and the capacitor 33, are positioned. A plurality of openings 36 are provided in the header 31 for receiving inputs to the A/D converters 23a–23n and outputs from the devices 14–17 and inputs to the devices 18a–18d and 19. Those of the openings which may not be utilized when providing to treat particular patients, may be closed by suitable plugs prior to implantation.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

What is claimed is:

1. A system for treating a malfunctioning heart comprising means for supplying a plurality of treatment modalities to a patient, a plurality of sensors for sensing respective parameters reflecting condition of a patient, means responsive to outputs from at least two of said sensors of at least two of said parameters reflecting condition of a patient for producing respective signal representations of the parameters, means for weighing the respective signal representations, means for processing output from the means for weighing to develop control output for selectively enabling the means for supplying a plurality of treatment modalities to a patient to effect selection of respective ones of treatment modalities as called for by the control output.

2. The system of claim 1, wherein the respective sensors comprise a first sensor for sensing mixed venous $O_2$ saturation and a second sensor for sensing activity level of a patient.

3. The system of claim 2, wherein the first sensor is positionable in the right ventricle of a heart.

4. The system of claim 2, wherein the first sensor is positionable in the right atrium of a heart.

5. The system of claim 2, wherein said second sensor comprises an accelerometer positionable to respond to motion of a patient.

6. The system of claim 1, wherein one of said at least two sensors comprises a temperature sensor positionable within an interior portion of the body of a patient.

7. The system of claim 1, wherein one of said at least two sensors comprises a temperature sensor positionable to sense temperature of blood within an interior portion of the body of a patient.

8. The system of claim 1, wherein one of said at least two sensors comprises a pH sensor operatively positionable to sense pH of blood at a site within the circulatory system of a patient.

9. The system of claim 1, wherein one of said at least two sensors is a pressure sensor.

10. The system of claim 9, wherein said means for producing signal representations includes means responsive to output from the pressure sensor for producing a signal representation of right ventricle pulse pressure.

11. The system of claim 9, wherein said means for producing signal representations includes means responsive to output from the pressure sensor for producing a signal representation of right ventricular systolic pressure.

12. The system of claim 9, wherein said means for producing signal representations includes means responsive to output from the pressure sensor for producing a signal representation of right atrial pressure.

13. The system of claim 9, wherein said means for producing signal representations includes means responsive to output from the pressure sensor for producing a signal representation of rapid change in arterial pressure.

14. The system of claim 1, wherein said at least two sensors comprise a first sensor for sensing mixed venous $O_2$ saturation and a second sensor for sensing a temperature of a patient.

15. The system of claim 14, wherein said second sensor is a temperature sensor positionable within an interior body portion of a patient.

16. The system of claim 14, wherein said second sensor is a temperature sensor positionable to sense temperature of blood of a patient.

17. A system for treating a malfunctioning heart comprising means for supplying a plurality of treatment modalities to a patient; means for producing respective signal representations of at least two parameters reflecting condition of a patient, said means for producing respective signal representations including means for providing a baseline signal for at least one of the at least two parameters; means for developing a short term signal of the at least one parameter and means for comparing the short term signal of the at least one parameter with the baseline signal to develop a difference signal as a function of the at least one parameter; means for weighing the difference signal function of the at least one parameter and remaining respective signal representations of at least the other parameter, means for processing output from the means for weighing to develop control output for selectively enabling the means for supplying a plurality of treatment modalities to the patient to effect selection of respective ones of treatment modalities as called for by the control output.

18. The system of claim 17, wherein said means for providing a baseline signal comprise means for providing a varying long term baseline signal for at least one of the parameters against which the short term signal is compared to develop the difference signal function of the at least one parameter.

19. The system of claim 17, wherein said means for providing a baseline signal comprises means for providing a varying long term baseline signal for at least one of the parameters against which the short term signal is compared to develop a ratio thereof as the function of the at least parameter.

20. A system for treating a malfunctioning heart comprising means for supplying a plurality of treatment modalities to a patient; means for producing respective signal representations of at least two parameters reflecting condition of a patient, said means for producing respective signal representations including means for providing a baseline signal for at least one of the parameters, means for developing a short term signal of the at least one parameter and means for comparing the short term signal of the at least one parameter to develop a ratio signal thereof as a function of the at least one parameter; and means for weighing the ratio signal function of the at least one parameter and remaining respective signal representations of the at least other parameters, means for processing output from the means for weighing to develop control output for selectively enabling the means for supplying a plurality of treatment modalities to the patient to effect selection of respective ones of treatment modalities as called for by the control output.

21. A method of treating a malfunctioning heart comprising, determining at least two parameters reflective of condition of a patient, weighing the respective determined parameters, algebraically summing the weighted parameters, and treating a patient with respective treatment modalities in accordance with the magnitude of the algebraic sum.

22. The method of claim 21, wherein the step of determining at least two parameters comprise determining mixed venous $O_2$ saturation and determining activity level of the patient.

23. The method of claim 22, wherein the step of determining mixed venous $O_2$ saturation comprises determining mixed venous $O_2$ saturation in the right ventricle of the heart of a patient.

24. The method of claim 22, wherein the step of determining mixed venous $O_2$ saturation comprises determining mixed venous $O_2$ saturation in the right atrium of a patient.

25. The method of claim 21, wherein the step of determining at least two parameters comprises determining the intensity of movement of the patient.

26. The method of claim 21, wherein the step of determining at least two parameters comprises determining temperature of an interior portion of the body of a patient.

27. The method of claim 21, wherein the step of determining at least two parameters comprises determining temperature of blood within an interior portion of the body of a patient.

28. The method of claim 21, wherein the step of determining at least two parameters comprises determining pH of blood within a patient.

29. The method of claim 21, wherein the step of determining at least two parameters comprises determining pressure at a site of the circulatory system of a patient.

30. The method of claim 29, wherein the step of determining pressure comprises determining right ventricular pulse pressure.

31. The method of claim 29, wherein the step of determining pressure comprises determining right ventricular systolic pressure.

32. The method of claim 29, wherein the step of determining pressure comprises determining right atrial pressure.

33. The method of claim 29, wherein the step of determining pressure comprises determining rapid change in arterial pressure.

34. The method of claim 21, wherein the step of determining at least two parameters comprise determining mixed venous blood $O_2$ saturation and determining temperature of the patient.

35. The method of claim 34, wherein the step of determining temperature comprises determining temperature of an interior body portion of the patient.

36. The method of claim 34, wherein the step of determining temperature comprises determining blood temperature of the patient.

37. The method of claim 21, including providing a baseline for at least one of the parameters, determining magnitude of the at least one parameter on a short term basis and determining the difference between the baseline and short term magnitude of the parameter as the function of the at least one parameter prior to weighing.

38. A method for treating a malfunctioning heart comprising, determining at least two parameters reflective of condition of a patient, providing a varying long term baseline of the at least one parameter based on variation of the parameter over a long term, determining magnitude of the at least one parameter on a short term basis and determining the difference between the varying baseline and the magnitude of the parameter as the function of the at least one parameter prior to weighing, weighing the respective determined parameters, algebraically summing the weighted parameters and treating a patient with respective treatment modalities in accordance with the magnitude of the algebraic sum.

39. A method of treating a malfunctioning heart comprising, determining at least two parameters reflective of condition of a patient, providing a baseline for at least one of the parameters, determining magnitude of the at least one parameter on a short term basis and determining the ratio of the baseline to the short term magnitude of the parameter as the function of the at least one parameter, weighing the determined ratio and respective ones of the determined other parameter or parameters, algebraically summing the weighted ratio and the other weighted parameter or parameters and treating a patient with respective treatment modalities in accordance of the magnitude of the algebraic sum.

40. A method for treating a malfunctioning heart comprising, determining at least two parameters reflective of condition of a patient, providing a varying long term baseline of the at least one parameter based on variation of the parameter over a long term, determining magnitude of the at least one parameter on a short term basis and determining the ratio of the varying baseline to the magnitude of the parameter as the function of the at least one parameter prior to weighing, weighing the respective determined parameters, algebraically summing the weighted parameters and treating a patient with respective treatment modalities in accordance with the magnitude of the algebraic sum.

41. A system for treating a malfunctioning heart comprising means for supplying a plurality of treatment modalities to a patient including cardioversion/defibrillation; means for sensing activity level of a patient; means for sensing heart rate of the patient; means, responsive to outputs from said means for sensing activity level and said means for sensing heart rate, for developing respective controlling outputs reflective of condition of the patient for selectively enabling said means for supplying a plurality of treatment modalities to said patient to effect selection of respective ones of treatment modalities as called for by the controlling outputs.

* * * * *